US012779074B2

(12) United States Patent
Hamberg et al.

(10) Patent No.: US 12,779,074 B2
(45) Date of Patent: Nov. 3, 2026

(54) BIOLOGICAL INDICATOR READER, SYSTEM AND METHODS OF USE

(71) Applicant: Crosstex International, Inc., Hauppauge, NY (US)

(72) Inventors: Keith Hamberg, Excelsior, MN (US); John C. Houge, Maple Grove, MN (US); Greg Ingersoll, Minneapolis, MN (US); Michael Scheidnes, Maple Grove, MN (US); Jeanette Sterner, Burnsville, MN (US); Thomas Strele, Phoenix, AZ (US)

(73) Assignee: CROSSTEX INTERNATIONAL, INC., Northbrook, IL (US)

( * ) Notice: Subject to any disclaimer, the term of this patent is extended or adjusted under 35 U.S.C. 154(b) by 547 days.

(21) Appl. No.: 18/259,821

(22) PCT Filed: Dec. 22, 2021

(86) PCT No.: PCT/US2021/064816
§ 371 (c)(1),
(2) Date: Jun. 29, 2023

(87) PCT Pub. No.: WO2022/150191
PCT Pub. Date: Jul. 14, 2022

(65) Prior Publication Data

US 2024/0066169 A1 Feb. 29, 2024

Related U.S. Application Data

(60) Provisional application No. 63/134,432, filed on Jan. 6, 2021, provisional application No. 63/134,429, filed
(Continued)

(51) Int. Cl.
*A61L 2/28* (2006.01)
*A61L 2/10* (2006.01)
(Continued)

(52) U.S. Cl.
CPC *A61L 2/28* (2013.01); *A61L 2/10* (2013.01); *A61L 2/24* (2013.01); *C12Q 1/22* (2013.01);
(Continued)

(58) Field of Classification Search
CPC ..... A61L 2/28; A61L 2/10; A61L 2/24; A61L 2202/11; A61L 2202/14; A61L 2103/15;
(Continued)

(56) References Cited

U.S. PATENT DOCUMENTS 4,448,534 A 5/1984 Wertz et al.
5,334,841 A 8/1994 Graessle et al.
(Continued)

FOREIGN PATENT DOCUMENTS

EP 0055027 A2 6/1982
WO 2005036128 A2 4/2005
(Continued)

OTHER PUBLICATIONS

International Preliminary Report on Patentability dated Jul. 20, 2023, of International PCT Application No. PCT/US/2021/064816 dated Dec. 22, 2021.
(Continued)

*Primary Examiner* — Regina M Yoo
(74) *Attorney, Agent, or Firm* — MARSHALL, GERSTEIN & BORUN LLP

(57) ABSTRACT

A biological indicator reader is provided for reading a plurality of biological indicators to determine the effectiveness of at least a sterilization process. Each biological indicator is configured to exhibit fluorescence when the sterilization process has failed. Each reader comprises a housing having a plurality of biological indicator holders, a heater coupled to the housing and configured to heat the plurality of biological indicator holders to a preselected temperature to incubate the biological indicators, a UV light
(Continued)

emitter configured to emit UV light through a first aperture on the side of each holder and an optical detector positioned under a second aperture on the bottom of the biological indicator holder, the optical detector configured to detect fluorescence intensity indicating the effectiveness of the sterilization process. A method of using the biological indicator reader is provided. A biological indicator system is also provided.

1 Claim, 10 Drawing Sheets

Related U.S. Application Data on Jan. 6, 2021, provisional application No. 63/134,433, filed on Jan. 6, 2021.

(51) Int. Cl.

| | |
|---|---|
| ***A61L 2/24*** | (2006.01) |
| ***C12Q 1/22*** | (2006.01) |
| ***G01N 21/64*** | (2006.01) |
| ***G01N 21/77*** | (2006.01) |

(52) U.S. Cl.

CPC ..... *G01N 21/6428* (2013.01); *G01N 21/6486* (2013.01); *G01N 21/77* (2013.01); *A61L 2202/11* (2013.01); *A61L 2202/14* (2013.01); *G01N 2021/6439* (2013.01); *G01N 2201/062* (2013.01)

(58) Field of Classification Search

CPC .. C12Q 1/22; G01N 21/6428; G01N 21/6486; G01N 21/77; G01N 2021/6439; G01N 2201/062; G01N 2021/7786; G01N 21/94; C12M 37/06

See application file for complete search history.

(56) References Cited

U.S. PATENT DOCUMENTS

| | | | | |
|---|---|---|---|---|
| 5,500,184 | A | 3/1996 | Palmer | |
| 5,736,355 | A | 4/1998 | Dyke et al. | |
| 5,739,004 | A | 4/1998 | Woodson | |
| 5,770,393 | A | 6/1998 | Dalmasso et al. | |
| 5,795,730 | A | 8/1998 | Tautvydas | |
| 5,801,010 | A | 9/1998 | Falkowski et al. | |
| 5,858,769 | A | 1/1999 | Diguiseppi et al. | |
| 5,863,790 | A | 1/1999 | Bolea | |
| 6,025,189 | A * | 2/2000 | Bolea | C12Q 1/22 435/31 |
| 6,037,598 | A | 3/2000 | Cicha | |
| 6,329,207 | B1 | 12/2001 | Fricker et al. | |
| 6,436,659 | B1 | 8/2002 | Hui et al. | |
| 6,485,978 | B1 | 11/2002 | Kirckof et al. | |
| 6,485,979 | B1 | 11/2002 | Kippenhan et al. | |
| 6,524,846 | B1 | 2/2003 | Robinson, Jr. | |
| 6,528,277 | B1 | 3/2003 | Hendricks et al. | |
| 6,541,777 | B1 | 4/2003 | Lombardo et al. | |
| 6,592,816 | B1 | 7/2003 | Ebel et al. | |
| 6,623,955 | B2 | 9/2003 | Matner et al. | |
| 6,791,092 | B2 | 9/2004 | Hamilton | |
| 6,884,394 | B1 | 4/2005 | Hehenberger et al. | |
| 6,924,139 | B2 | 8/2005 | Eveland et al. | |
| 7,122,150 | B2 | 10/2006 | Gonzalez et al. | |
| 7,247,482 | B2 | 7/2007 | Lemus et al. | |
| 7,326,562 | B2 | 2/2008 | Felkner et al. | |
| 7,483,805 | B2 | 1/2009 | Sparks et al. | |
| 7,563,616 | B2 | 7/2009 | Gillis et al. | |
| 7,670,552 | B2 | 3/2010 | Read | |
| 7,790,105 | B2 | 9/2010 | Bala | |
| 7,899,681 | B2 | 3/2011 | Katzenmaier et al. | |
| 7,968,854 | B2 | 6/2011 | Hormann | |
| 8,173,388 | B2 | 5/2012 | Pasmore et al. | |
| 8,283,133 | B2 | 10/2012 | Franciskovich et al. | |
| 8,343,768 | B2 | 1/2013 | Kyung-Hee Song et al. | |
| 8,394,344 | B2 | 3/2013 | Schutt et al. | |
| 8,546,132 | B1 | 10/2013 | Lewis et al. | |
| 8,652,412 | B2 | 2/2014 | Hyde et al. | |
| 8,858,884 | B2 | 10/2014 | Franciskovich et al. | |
| 8,906,693 | B2 | 12/2014 | Schultz et al. | |
| 8,969,029 | B2 | 3/2015 | Chandrapati et al. | |
| 9,012,209 | B2 | 4/2015 | Eden et al. | |
| 9,068,976 | B2 | 6/2015 | Putnam et al. | |
| 9,121,050 | B2 | 9/2015 | Franciskovich et al. | |
| 9,145,573 | B2 | 9/2015 | Pederson et al. | |
| 9,186,430 | B2 | 11/2015 | Dane et al. | |
| 9,207,180 | B2 | 12/2015 | Eden | |
| 9,303,283 | B2 | 4/2016 | Franciskovich et al. | |
| 9,316,590 | B2 | 4/2016 | Chang et al. | |
| 9,410,180 | B2 | 8/2016 | Pederson et al. | |
| 9,428,786 | B2 | 8/2016 | Pederson et al. | |
| 9,540,677 | B2 | 1/2017 | Smith et al. | |
| 9,687,575 | B2 | 6/2017 | Farren | |
| 9,701,996 | B2 | 7/2017 | Smith et al. | |
| 10,047,334 | B2 | 8/2018 | Chandrapati et al. | |
| 10,059,977 | B2 | 8/2018 | Witcher et al. | |
| 10,195,299 | B2 | 2/2019 | Baker et al. | |
| 10,443,083 | B2 | 10/2019 | Eghbal et al. | |
| 10,632,220 | B2 | 4/2020 | Fang et al. | |
| 2001/0021356 | A1 | 9/2001 | Konrad | |
| 2002/0058296 | A1 | 5/2002 | Miller et al. | |
| 2002/0162970 | A1 | 11/2002 | Sasges | |
| 2004/0197848 | A1 | 10/2004 | Behun et al. | |
| 2004/0200975 | A1 | 10/2004 | Brown et al. | |
| 2006/0263258 | A1 | 11/2006 | Harris et al. | |
| 2008/0297864 | A1 | 12/2008 | Horgan et al. | |
| 2011/0210257 | A9 | 9/2011 | Handique et al. | |
| 2013/0230910 | A1 | 9/2013 | Christensen et al. | |
| 2013/0273594 | A1 | 10/2013 | Ahimou et al. | |
| 2014/0271370 | A1 | 9/2014 | Sirotin et al. | |
| 2014/0370535 | A1 | 12/2014 | Chandrapati et al. | |
| 2015/0147408 | A1 | 5/2015 | Berry et al. | |
| 2015/0335777 | A1 | 11/2015 | Robbins et al. | |
| 2016/0109337 | A1 | 4/2016 | Valkenier et al. | |
| 2017/0023555 | A1 | 1/2017 | Ou et al. | |
| 2017/0037447 | A1 | 2/2017 | Chandrapati et al. | |
| 2017/0247742 | A1 | 8/2017 | Doyle et al. | |
| 2018/0015193 | A1 | 1/2018 | Swaminathan et al. | |
| 2018/0104015 | A1 | 4/2018 | Bryant et al. | |
| 2018/0237821 | A1 | 8/2018 | Fryer | |
| 2018/0245122 | A1 | 8/2018 | Soto et al. | |
| 2018/0252701 | A1 | 9/2018 | Rhodes et al. | |
| 2018/0355400 | A1 | 12/2018 | Centanni et al. | |
| 2019/0002951 | A1 | 1/2019 | Fryer et al. | |
| 2019/0017091 | A1 | 1/2019 | Centanni et al. | |
| 2019/0017092 | A1 | 1/2019 | Franciskovich et al. | |
| 2019/0017093 | A1 | 1/2019 | Franciskovich et al. | |
| 2019/0117810 | A1 | 4/2019 | Ludowise et al. | |
| 2019/0125912 | A1 | 5/2019 | Bommarito et al. | |
| 2019/0169672 | A1 | 6/2019 | Fryer et al. | |
| 2020/0199516 | A1 | 6/2020 | Rhodes et al. | |

FOREIGN PATENT DOCUMENTS

| | | | | |
|---|---|---|---|---|
| WO | WO-2006086547 | A2 * | 8/2006 | A61L 2/28 |
| WO | 2018025207 | A1 | 2/2018 | |
| WO | 2019164075 | A1 | 8/2019 | |
| WO | 2020023833 | A1 | 1/2020 | |
| WO | 2020128959 | A1 | 6/2020 | |
| WO | 2020136608 | A1 | 7/2020 | |
| WO | 2020136613 | A1 | 7/2020 | |
| WO | 2020183433 | A1 | 9/2020 | |
| WO | 2020183434 | | 9/2020 | |
| WO | 2022150191 | A1 | 7/2022 | |

(56) References Cited

FOREIGN PATENT DOCUMENTS

| | | | |
|---|---|---|---|
| WO | 2022150192 | A1 | 7/2022 |
| WO | WO2022150193 | A1 | 7/2022 |

OTHER PUBLICATIONS

International Preliminary Report on Patentability dated Jul. 20, 2023, of International PCT Application No. PCT/US/2021/064818 dated Dec. 22, 2021.

International Preliminary Report on Patentability dated Jul. 20, 2023, of International PCT Application No. PCT/ US/2021/064821 dated Dec. 22, 2021.

International Search Report and Written Opinion of the International Searching Authority Dated Mar. 15, 2022, of International PCT Application No. PCT/US2021/064816 filed Dec. 22, 2021.

International Search Report and Written Opinion of the International Searching Authority Dated Mar. 16, 2022, of International PCT Application No. PCT/US2021/064818 filed Dec. 22, 2021.

International Search Report and Written Opinion of the International Searching Authority Dated Mar. 25, 2022, of International PCT Application No. PCT/US2021/064621 filed Dec. 22, 2021.

* cited by examiner

BIOLOGICAL INDICATOR READER, SYSTEM AND METHODS OF USE

CROSS REFERENCE TO RELATED APPLICATIONS

This application claims priority to U.S. Provisional Patent Application with Ser. No. 63/134,429 filed, Jan. 6, 2021, and claims priority to U.S. Provisional Patent Application with Ser. No. 63/134,432 filed Jan. 6, 2021, and claims priority to U.S. Provisional Patent Application with Ser. No. 63/134,433 filed Jan. 6, 2021. These applications are incorporated herein by reference, in their entireties.

BACKGROUND

Sterilization is a process conducted in a specially designed chamber or sterilizer that results hopefully in a complete eradication of all viable microorganisms that may be living on medical, dental or surgical instruments. Sterilization techniques have evolved over time from the traditional methods employing saturated steam at elevated temperature and ethylene oxide gases to more modern techniques such as those employing liquid, vapor, and plasma. The effectiveness of the sterilization process must be evaluated regardless of the technique used especially when a medical, dental or surgical instrument is going to be used on or in the human body.

Biological indicators are devices that are used to test the efficacy of sterilization chambers such as those employed in healthcare facilities and laboratories for sterilizing medical, dental or surgical instruments. A biological indicator provides information on whether necessary conditions were met to kill a specified number of microorganisms for a given sterilization process, which provides the user a certain level of confidence in their particular sterilization process.

A typical biological indicator being used today is a self-contained biological indicator (SCBI), which contains, among other things, microorganisms, culture medium, carrier, and a crushable container (e.g., vial). After the biological indicator is exposed to a sterilization process, the crushable container of the biological indicator is crushed or activated and placed in a biological indicator reader, which has, among other things, an incubator, a UV light emitter and an optical detector.

Any microorganism remaining in the biological indicator, after the sterilization process, is incubated in the culture medium after the indicator is activated. Metabolism of the culture medium by viable microorganisms surviving in the medium will cause a fluorescent signal on exposure of the medium to UV light. This fluorescent signal, if intense enough, will be detected by the optical detector indicating a sterilization failure during the sterilization process, where the proper conditions (e.g., time, temperature, position in the sterilizer, etc.) for sterilization were not met. Medical, dental or surgical instruments not properly sterilized can potentially contaminate patients if used.

Unfortunately, some biological indicator readers currently available provide inaccurate results on whether the proper conditions were met to kill a specified number of microorganisms for a given sterilization process. These biological indicator readers fail to provide the user with confidence that the proper sterilization process has occurred. Thus, there is a need for an improved biological indicator reader, system, and method, which reduce inaccurate results of the sterilization process.

SUMMARY

A biological indicator (BI) reader is provided that reduces inaccurate results of the sterilization process. In one embodiment, there is a biological indicator (BI) reader for reading a plurality of biological indicators to determine the effectiveness of at least a sterilization process. Each biological indicator is configured to exhibit increased fluorescence when the sterilization process has failed. Each BI reader comprises a housing having a plurality of biological indicator holders, each holder configured to receive one of the plurality of biological indicators, each biological indicator holder having a first aperture on a side and a second aperture on a bottom of the biological indicator holder. The biological indicator reader also includes a heater which is coupled to the housing and configured to heat the plurality of biological indicator holders to a preselected temperature to incubate the biological indicators. The biological indicator reader further includes a UV light emitter configured to emit UV light incident upon a BI through a first aperture on the side of each BI holder and an optical detector positioned under a second aperture directly below the bottom of the biological indicator holder, the optical detector configured to detect fluorescence intensity indicating the effectiveness of the sterilization process.

A method for determining the effectiveness of at least a sterilization process is also provided. The method comprises providing a biological indicator reader for reading a plurality of biological indicators to determine the effectiveness of at least a sterilization process, each biological indicator configured to exhibit fluorescence when the sterilization process has failed, the reader comprising a housing having a plurality of biological indicator holders, each holder configured to receive one of the plurality of biological indicators, each biological indicator holder having a first aperture on a side and a second aperture on a bottom of the biological indicator holder; a heater coupled to the housing and configured to heat the plurality of biological indicator holders to a preselected temperature to incubate the biological indicators; a UV light emitter configured to emit UV light through the first aperture on the side of each biological indicator holder; an optical detector positioned under the second aperture on the bottom of the biological indicator holder, the optical detector configured to detect fluorescence intensity indicating the effectiveness of the sterilization process.

The method also includes providing a biological indicator capable of exhibiting fluorescence to indicate the effectiveness of a sterilization process, the biological indicator comprising a crushable container; subjecting the biological indicator to the sterilization process to obtain a sterilized biological indicator; crushing the crushable container of the sterilized biological indicator to activate the biological indicator; incubating the activated biological indicator in one of the biological indicator holders of the biological indicator at a preselected temperature and for a preselected period of time; emitting UV light through the first aperture on the side of each biological indicator holder; and detecting fluorescence intensity by the optical detector indicating the effectiveness of the sterilization process.

A biological indicator system for detecting the effectiveness of a sterilization process is also provided. In many aspects, the system described in this disclosure comprises a biological indicator reader for reading a plurality of biological indicators to determine the effectiveness of at least a sterilization process, each biological indicator configured to exhibit fluorescence when the sterilization process has failed. In some embodiments, the biological indicator reader comprises a housing having a plurality of biological indicator holders, each holder configured to receive one of the plurality of biological indicators. In other embodiments, each biological indicator holder has a first aperture on a side of the biological indicator holder and a second aperture on a bottom of the biological indicator holder. The biological indicator reader also includes a heater coupled to the housing and configured to heat the plurality of biological indicator holders to a preselected temperature and a preselected period of time to incubate the biological indicators; a UV light emitter configured to emit UV light through the first aperture on the side of each holder; and an optical detector positioned under the second aperture on the bottom of the biological indicator holder, the optical detector configured to detect fluorescence intensity indicating the effectiveness of the sterilization process; and a biological indicator containing spores, growth media containing a fluorescent moiety and a crushable container, the biological indicator being sterilizable and configured to receive UV light from the UV light emitter.

While multiple embodiments are disclosed, still other embodiments of the present disclosure will become apparent to those skilled in the art from the following detailed description, which shows and describes illustrative embodiments of the disclosure. As will be realized, the various embodiments of the present disclosure are capable of modifications in various obvious aspects, all without departing from the spirit and scope of the present disclosure. Accordingly, the detailed description is to be regarded as illustrative in nature and not restrictive.

BRIEF DESCRIPTION OF DRAWINGS

In part, other aspects, features, benefits and advantages of the embodiments will be apparent with regard to the following description, appended claims and accompanying drawings where:

Figure 1:
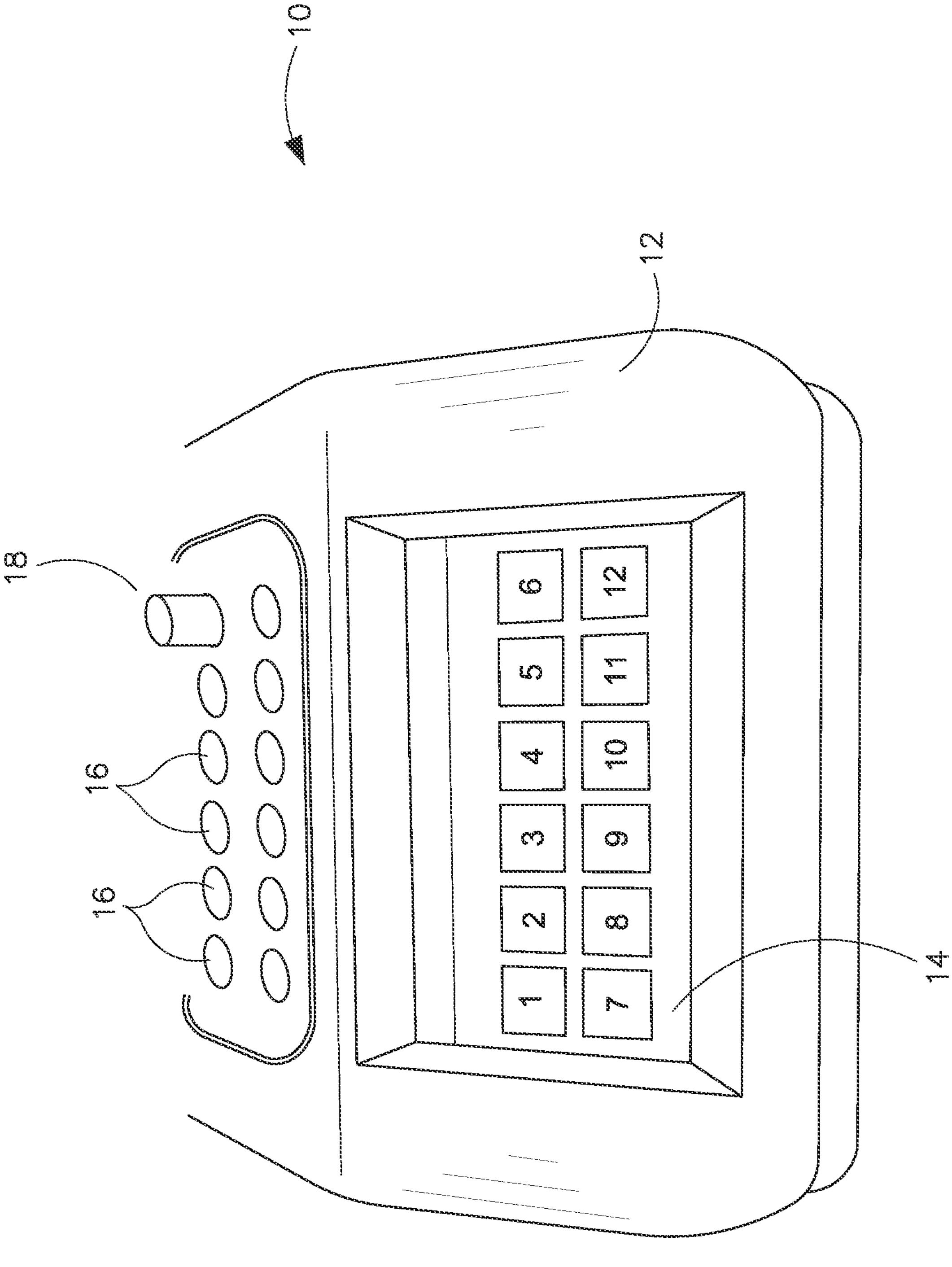
FIG. 1 is a perspective view of a biological indicator reader according to one embodiment of the present disclosure, the biological indicator reader comprising at least one biological indicator positioned in each biological indicator holder.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the embodiments are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a vial" includes one, two, three or more vials.

DEFINITIONS

The term "sterilization" includes, but is not limited to, rendering a substance incapable of reproduction, metabolism and/or growth. While this is often taken to mean total absence of living organisms, the term may also be used to refer to a substance free from living organisms to a degree previously agreed to be acceptable. Unless otherwise indicated, the term sterilization may also include methods and procedures less rigorous than sterilization, for example, disinfection, sanitization, or the like. The sterilization indicator or biological indicator and the methods, and apparatus described herein may be used in health care fields, scientific fields, or the like. These may be used in commercial and industrial applications where sterilization, disinfection, sanitization, or the like, may be desired, for example, sterilization, disinfection and sanitization of medical, dental and/or surgical instruments and/or implants, food processing, pharmaceutical manufacturing, or the like.

The biological indicator or sterilization indicator described may be used in any sterilization process. These may include sterilization processes where the sterilization medium or sterilant may be steam or dry heat, as well as one or more gaseous sterilants, one or more liquid sterilants, or the like. The gaseous sterilants may comprise ethylene oxide, gaseous hydrogen peroxide, gaseous peracetic acid or the like. The liquid sterilants may comprise formalin (formaldehyde gas dissolved in water and optionally containing methanol to inhibit the formation of toxic substances), glutaraldehyde, peracetic acid, liquid hydrogen peroxide, or the like.

The sterilization indicator or biological indicator may be used to examine the lethality of sterilants against any microorganism with less resistance to the sterilization process.

The term "microorganism" or "microorganisms" refers to bacteria, viruses or fungi. The microorganism can be in a spore form or vegetative state. In some embodiments, *Bacillus, Clostridium, Neurospora*, and/or *Candida* species of microorganisms are applied to the SCBI. In various embodiments, *Bacillus* and *Clostridia* species are used to monitor sterilization processes utilizing saturated steam, dry heat, gamma irradiation, and ethylene oxide. In some embodiments, microorganisms such as *Geobacillus stearothermophilus* and *Bacillus atrophaeus* monitor sterilization conditions. *Geobacillus stearothermophilus* is particularly useful to monitor sterilization under steam sterilization conditions. In various embodiments, microorganisms may include bacteria such as *Escherichia coli, Legionella* sp., *Campylobacter* sp., and other enteric bacteria. The bacteria can include *Staphylococcus* and *Streptococcus* species and other human pathogenic microorganisms such as *Cryptosporidium.*

The term "spore" refers to an asexual reproductive cell capable of developing into a new individual without fusion with another reproductive cell. The term "spore" is used throughout the present disclosure for simplicity, but it should be understood that microorganisms (e.g., bacteria, fungi, viruses, etc.), spores (e.g., bacterial, fungal, etc.), enzymes, substrates for enzymatic activity, ATP, microbial metabolites, or a combination thereof, can be used in the biological indicator of the present disclosure. In one aspect, the spores of the present disclosure are produced by bacteria and fungi. Bacterial spores serve largely as a resting, or dormant stage in the bacterial life cycle, serving to preserve the bacterium through periods of unfavorable conditions. Many bacterial spores are highly durable and can germinate even after years of dormancy. The bacterial spore is recognized as the most resistant form of microbial life. It is the life form of choice in all tests for determining the sterilizing efficacy of devices, implants, chemicals and processes. In one embodiment, one way of detecting whether bacteria are still present on a carrier of the biological indicator is through enzyme activity. The enzyme alpha-D-glucosidase has been identified in spores of *Geobacillus stearothermophilus*, such as those commercially available as "ATCC 7953" from American Type Culture Collection, Rockville, MD. *Bacillus atrophaeus* is particularly useful to monitor conditions of gas and dry heat sterilization. The enzyme beta-D-glucosidase has been found in *Bacillus atrophaeus* (e.g., commercially available as "ATCC 9372" from American Type Culture Collection). In various embodiments, the spores comprise *Bacillus, Clostridium, Neurospora, Candida*, and, and/or *Cryptosporidium*. In some embodiments, the spores comprise *Geobacillus stearothermophilus* and/or *Bacillus atrophaeus.*

The term "endospore" refers to a dormant, tough, and non-reproductive structure produced by certain bacteria from the Firmicute phylum. Examples of endospores include, but are not limited to, *Geobacillus stearothermophilus, Bacillus subtilis, Bacillus subtilis globigii, Bacillus atrophaeus, Clostridium sporogenes, Bacillus cereus*, and *Bacillus circulans*. Examples of fungi include *Aspergillus niger, Candida albicans, Trichophyton mentagrophytes*, and *Wangiella* dermatitis. Examples of mycobacteria which can be utilized in the present disclosure include *Mycobacterium chelonae, Mycobacterium gordonae, Mycobacterium smegmatis*, and *Mycobacterium terrae.*

The term "vegetative bacteria" refers to a state of bacteria in which growth and reproduction occurs and where spore formation does not occur. Examples of vegetative bacteria include, but are not limited to, *Aeromonas hydrophila, Enterococcus faecalis, Streptococcus faecalis, Enterococcus faecium, Streptococcus pyrogenes, Escherichia coli, Klebsiella* (*pneumoniae*), *Legionella pneumophila, Methylobacterium, Pseudomonas aeruginosa, Salmonella choleraesuis, Helicobacter pylori, Staphylococcus aureus, Staphylococcus epidermidis*, and *Stenotrophomonas maltophilia.*

The phrase "biological activity" generally refers to any specific catalytic process or groups of processes associated with a biological cell. Nonlimiting examples of biological activities include catabolic enzyme activities (e.g., carbohydrate fermentation pathways), anabolic enzyme activities (e.g., nucleic acid, amino acid, or protein synthesis), coupled reactions (e.g., a metabolic pathway), biomolecule-mediated redox reactions (e.g., electron transport systems), and bioluminescent reactions. "Predetermined" biological activity means that the method is directed toward the detection of a specific biological process (e.g., an enzyme reaction) or group of biological processes (e.g., a biochemical pathway). It will be appreciated by a person having ordinary skill in the art that certain predetermined biological activities may be associated with a particular type of cell (e.g., microorganism) or a pathological process.

Similarly, it should be understood that phrases used in the present disclosure that include the term "spore," such as "spore carrier," "spore reservoir," "spore region," "spore growth chamber," and the like, are used merely for simplicity, but that such components, elements or phrases equally apply to other sources of biological activity and are not intended to refer only to spores. For example, the above phrases can also be referred to as a "source carrier," a "source region," a "source reservoir," a "source growth chamber," and the like.

The process of bringing the spores and medium together can be referred to as "activation" of the biological indicator. That is, the term "activation" and variations thereof, when used with respect to a biological indicator, can generally refer to bringing spores of the biological indicator in sterilant communication with a liquid or medium (e.g., an aqueous mixture comprising a nutrient medium for the spores). For example, when a frangible container within the biological indicator that contains the medium is at least partially fractured, punctured, pierced, crushed, cracked, or the like, such that the medium has been put in sterilant communication with the spores, the biological indicator can be described as having been "activated." Said another way, a biological indicator has been activated when the spores have been exposed to the medium which was previously housed separately from the spores.

Suitable enzymes can include hydrolytic enzymes and/or enzymes derived from spore-forming microorganisms, such as *Bacillus stearothermophilus* and *Bacillus subtilis*. Enzymes from spore-forming microorganisms that can be useful in the biological indicators of the present disclosure can include beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, tyrosine aminopeptidase, phenylalanine aminopeptidase, beta-D-glucuronidase, alpha-L-arabinofuranosidase, N-acetyl-beta-glucosaminodase, beta-D-cellobiosidase, alanine aminopeptidase, proline aminopeptidase and fatty acid esterases.

Some embodiments of the biological indicator can include chromogenic and/or fluorogenic substrates that react with enzymes to form detectable products. These substrates may be classified in two groups based on the manner in which they create a visually detectable signal. The substrates in the first group react with enzymes to form enzyme-modified products that are themselves chromogenic or fluorescent. Substrates in the second group form enzyme-modified products that can react further with an additional compound, or compounds, to generate a color or fluorescent signal. Examples of fluorogenic substrates include, for example, 4-methylumbelliferyl-α-D-glucopyranoside (MUG) or para-nitrophenol-α-D-glucoside (PNPG). These include fluorescent moieties that when metabolized allow fluorescence and detection.

As a result, the phrase "detectable product" can refer to any molecule, compound, substance, substrate, or the like, or combinations thereof, that can be detected by any of the detection methods or processes described below. For example, such detectable products can be a sign of the viability of a source of biological activity, and detection of such products can generally indicate the failure or inadequacy of a sterilization process.

In some embodiments, the source of active enzyme can be (1) the purified, isolated enzyme derived from an appropriate microorganism; (2) a microorganism to which the enzyme is indigenous or added by genetic engineering; and/or (3) a microorganism to which the enzyme has been added during sporulation or growth, such that the enzyme is incorporated or associated with the microorganism, e.g., an enzyme added to a spore during sporulation which becomes incorporated within the spore. In some embodiments, the microorganisms which may be utilized as the source of an enzyme include bacteria or fungi in either the spore or vegetative state. In some embodiments, the enzyme source includes *Bacillus, Clostridium, Neurospora, Candida*, or a combination of such species of microorganisms.

The enzyme alpha-D-glucosidase has been identified in spores of *Bacillus stearothermophilus*, such as those commercially available as "ATCC 8005" and "ATCC 7953" from American Type Culture Collection, Rockville, Md. The enzyme beta-D-glucosidase has been found in *B. subtilis* (e.g., commercially available as "ATCC 9372" from American Type Culture Collection).

In the event that an isolated enzyme is utilized, or the microorganism used as the source of the enzyme is not more resistant to the sterilization conditions than the natural contaminants, another microorganism commonly used to monitor sterilization conditions can be exposed to the sterilization cycle along with the enzyme source. In such a case, the method of the present disclosure may include the step of incubating any viable microorganism remaining after the sterilization cycle with an aqueous nutrient medium to confirm the sterilization efficacy.

In general, monitoring the effectiveness of the sterilization process can include placing the biological indicator of the present disclosure in a sterilizer. In some embodiments, the sterilizer includes a sterilization chamber that can be sized to accommodate a plurality of articles to be sterilized and can be equipped with a means of evacuating air and/or other gases from the chamber and a means for adding a sterilant to the chamber. The biological indicator of the present disclosure can be positioned in areas of the sterilizer that are most difficult to sterilize (e.g., above the drain). Alternately, the biological indicator of the present disclosure can be positioned adjacent (or in the general proximity of) an article to be sterilized when the biological indicator is positioned in the sterilization chamber. In addition, the biological indicator can be positioned in process challenge devices that can be used in sterilizers.

The sterilization process can further include exposing the article(s) to be sterilized and the biological indicator to a sterilant. In some embodiments, the sterilant can be added to the sterilization chamber after evacuating the chamber of at least a portion of any air or other gas present in the chamber. Alternatively, sterilant can be added to the chamber without evacuating the chamber. A series of evacuation steps can be used to assure that the sterilant reaches all desired areas within the chamber and contacts all desired article(s) to be sterilized, including the biological indicator.

In general, after the biological indicator has been exposed to a sterilization cycle, a liquid (e.g., a growth media, water that can be mixed with a solid growth media, etc., or combinations thereof) can be introduced to the spores. As mentioned above, the step in which the liquid is introduced to the spores can be referred to as "activation" of the biological indicator or the "activation step." If the spores have survived the sterilization cycle, the liquid will facilitate metabolic activity and/or growth of the spores, and such activity and/or growth can be investigated. If growth is observed, the sterilization cycle is generally deemed ineffective.

Reference will now be made in detail to various embodiments of the present disclosure, examples of which are illustrated in the accompanying drawings. While the embodiments of the present disclosure will be described in conjunction with the illustrated embodiments, it will be understood that they are not intended to limit the disclosure to those embodiments. On the contrary, the disclosure is intended to cover all alternatives, modifications, and equivalents, which may be included within the disclosure as defined by the appended claims.

The headings below are not meant to limit the disclosure in any way; embodiments under any one heading may be used in conjunction with embodiments under any other heading.

Biological Indicator Reader

The biological indicator reader of this disclosure is designed, in one embodiment, to provide two primary functions, namely, incubating a biological indicator (BI) and detecting a possible sterilization failure. The incubation is typically conducted in a constant temperature BI holder or receiving BI holder at about 60° C. A small cylindrical BI is placed in the receiving BI holder to incubate the test sample (inside the BI) at 60° C. for a fixed amount of time, for example, about 30 minutes. During this time, an optical system, for example, a UV light emitter can expose the test sample to short bursts of ultra-violet light (UV), the optical system is configured to detect a fluorescent light signal from the sample. During alternate time intervals, when the UV light is off, the optical system is also configured to detect a fluorescent light signal from the sample. The difference between these two signals are data measured and recorded. The fluorescence is produced by an enzymatic reaction involving 4-methylumbelliferyl-α-D-glucopyranoside (MUG) or para-nitrophenol-α-D-glucoside (PNPG), which is associated with spore growth inside the self-contained BI. Over the duration of the test, if enough fluorescent signal is detected, the BI test is considered positive and a sterilization failure is detected. On the other hand, if the test has not detected enough fluorescent signal, the test is negative, and the sterilization is valid and confirmed.

The BI reader is one component of a larger Rapid Read Biological Indicator System (RRBIS) which comprises, consists essentially of or consists of the BI reader and multiple biological indicators (BI). The Rapid Read Biological Indicator System provides a rapid monitoring of steam sterilization processes performed at health care facilities. For example, a BI can be placed in the same sterilization environment as medical, dental or surgical instruments being sterilized. After the sterilization sequence is complete, the BI is then placed in the BI reader to verify that sterilization of the medical instruments was successful. If the BI sample is sterilized, then the medical instruments would also be sterilized. In some aspects, the BI reader is designed to incubate and automatically read a 3-hour rapid read BI for steam at about 60° C. for a final fluorescence result at about one (1) hour or less. In many aspects, the expected test time can be about 30 minutes. The BI reader is also designed to allow for further incubation of the above mentioned BI for a pH color change result after 48 hours. A positive fluorescence reading, or a pH color change indicates a steam sterilization process failure.

Examples of conventional biological indicators that can be used with the BI reader of the current disclosure are described in U.S. Pat. Nos. 5,252,484; 6,025,189; and 6,063,591, which are incorporated herein by reference as if set forth in full. As described in more detail in this application, the BI reader of this disclosure differs in many respects from conventional BI readers. Biological indicators that can be used in the BI reader of the current application can be obtained from Crosstex International, Inc. Hauppauge, New York, USA.

FIG. 1 illustrates a biological sterilization or indicator (BI) reader 10 according to one embodiment of the present disclosure. The BI reader 10 includes a housing 12, a display panel 14, twelve (12) receiving BI holders 16, each BI holder 16 dimensioned to receive at least a portion of a biological indicator 18.

As further illustrated in FIGS. 1-4A, 4B and 4C, in several embodiments, BI reader 10 comprises twelve (12) BI holders 16 each for receiving a BI 18. Each BI holder 16 operates independently. After the BI is removed from a sterilization chamber along with medical, dental and/or surgical instruments, after a sterilization process has occurred (not shown), the BI 18 is activated by crushing the vial to mix the carrier containing spores with the growth medium. The BI 18 is then placed in a BI holder 16 where, in some embodiments, a 30-minute countdown begins. In this embodiment, all twelve BI holders are maintained at a constant temperature of about 60° C., and the 30-minute countdown is the incubation period for the growth media 25 present on the BI carrier 28. At the end of the incubation period, UV light is emitted at the BI and the BI reader 10 will indicate a positive or negative result by the amount of fluorescent signal received from the BI carrier 28. The test result is then displayed on a display panel 14, which can be an LCD touch screen and a record of the test is added to a software file called the history log.

Figure 2:
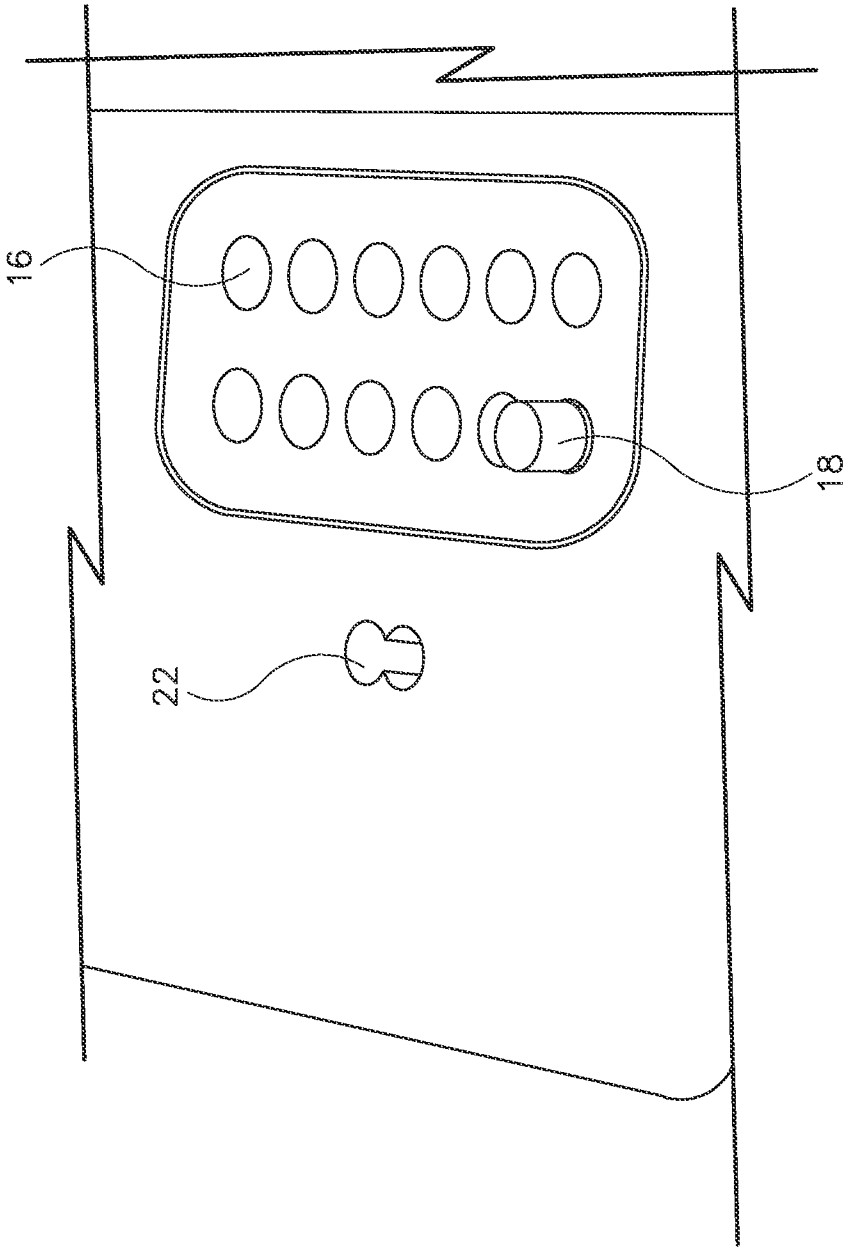
FIG. 2 is a top view of the biological indicator reader according to one embodiment of the present disclosure showing twelve (12) biological indicator holders and one (1) biological indicator crusher.
Figures 4A, 4B, 4C, 4D:
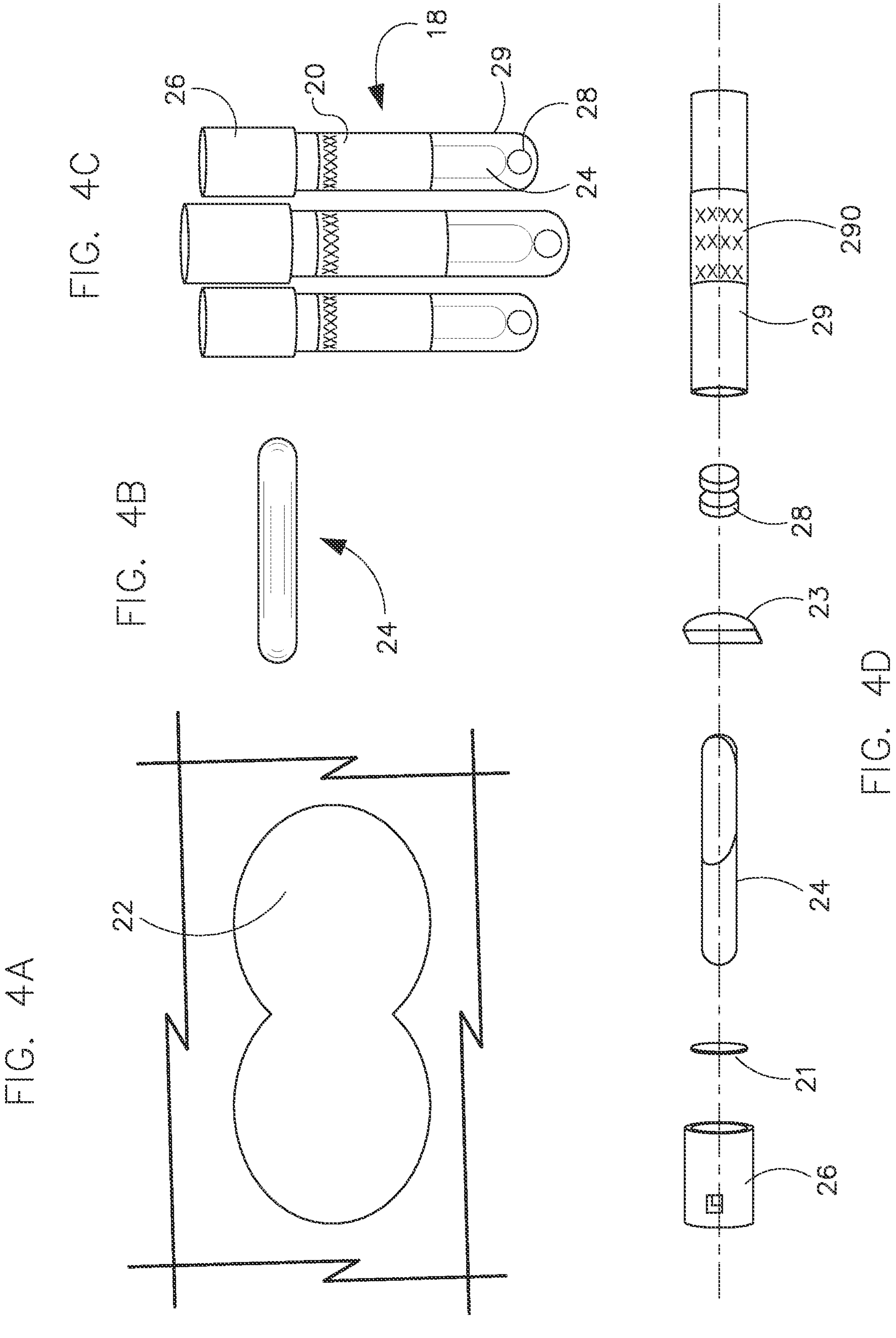
FIG. 4A is an enlarged view of a biological indicator crusher.
FIG. 4B is a perspective view of a growth media ampoule.
FIG. 4C is a perspective view of three (3) biological indicators.
FIG. 4D is a dissembled view of a biological indicator.

In many aspects of the present application, as illustrated in FIGS. 2, 4A and 4B, housing 12 of the BI reader 10 further comprises a BI crusher 22 disposed proximately to the biological indicator holders 16. BI crusher 22 is sized to crush the crushable ampoule 24 inside BI container 20 and release the growth medium 25 within each BI 18. In some aspects, BI reader 10 includes a cover (not shown) for the plurality of biological indicator holders 16. The BI reader 10 also contains a display panel 14 in FIG. 1, which is coupled to an electronic controller system 50 and is configured to provide an indication of the effectiveness of the sterilization process associated with each biological indicator. Although the electronic controller system 50 is shown as separate, it may be part of the housing or combined in one or more computer systems. Indeed, the electronic controller system may be one or more hardware, software, or hybrid components residing in (or distributed among) one or more local or remote computer systems. FIG. 4D illustrates an embodiment of a dissembled biological indicator. The biological indicator, or a BI vial comprises cap 26, cap filter 21, ampoule 24, BI carrier support 23, BI carrier 28, sleeve 29 and label 290. In some embodiments, the ampoule is a crushable glass media ampoule. The BI carrier can be a spore strip. In some embodiments, the BI carrier support can be a spore strip support. The sleeve can be a plastic sleeve containing the ampoule, BI carrier and BI carrier support. The label can contain information about the vial and/or the vial contents, which can be inputted into the BI reader. The plastic outer sleeve can be soft and pliable. To activate the BI vial, the glass ampoule is broken ("crushed") to allow the liquid media inside the ampoule to wet the spore strip. In some embodiments, a BI crusher is provided that can have a design to match the holders or wells of the BI reader. When placing a BI vial in the crusher, it is pushed from one side to the other to break the glass ampoule and activate the BI vial. When the ampoule liquid media makes contact with the spore strip, if the spores are still alive after a sterilization process, they produce a fluorophore byproduct, for example, a 4MU byproduct. If the BI spores are dead, then no fluorophore byproduct is produced.

It also should be readily apparent that the components of the biological indicator as described herein may be merely logical constructs or routines that are implemented as physical components combined or further separated into a variety of different components, sharing different resources (including processing units, memory, clock devices, software routines, logic commands, etc.) as required for the particular implementation of the embodiments disclosed. Indeed, even a single general purpose computer (or other processor-controlled device) executing a program stored on an article of manufacture (e.g., recording medium or other memory units) to produce the functionality referred to herein may be utilized to implement the illustrated embodiments. It also will be understood that a plurality of computers or servers can be used to allow the biological indicator to be a network based system having a plurality of computers linked to each other over the network or Internet or the plurality of computers can be connected to each other to transmit, edit, and receive data via cloud computers.

Figure 3B:
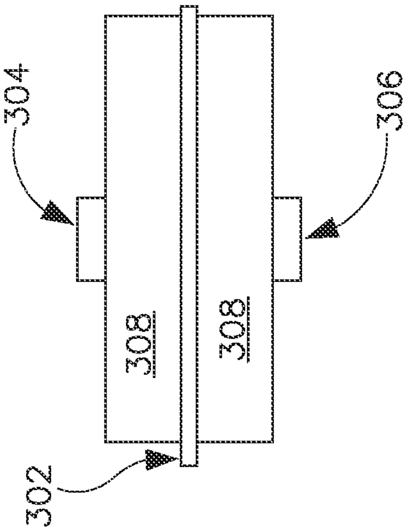
FIG. 3B illustrates an embodiment of a heater control.
Figure 3A:
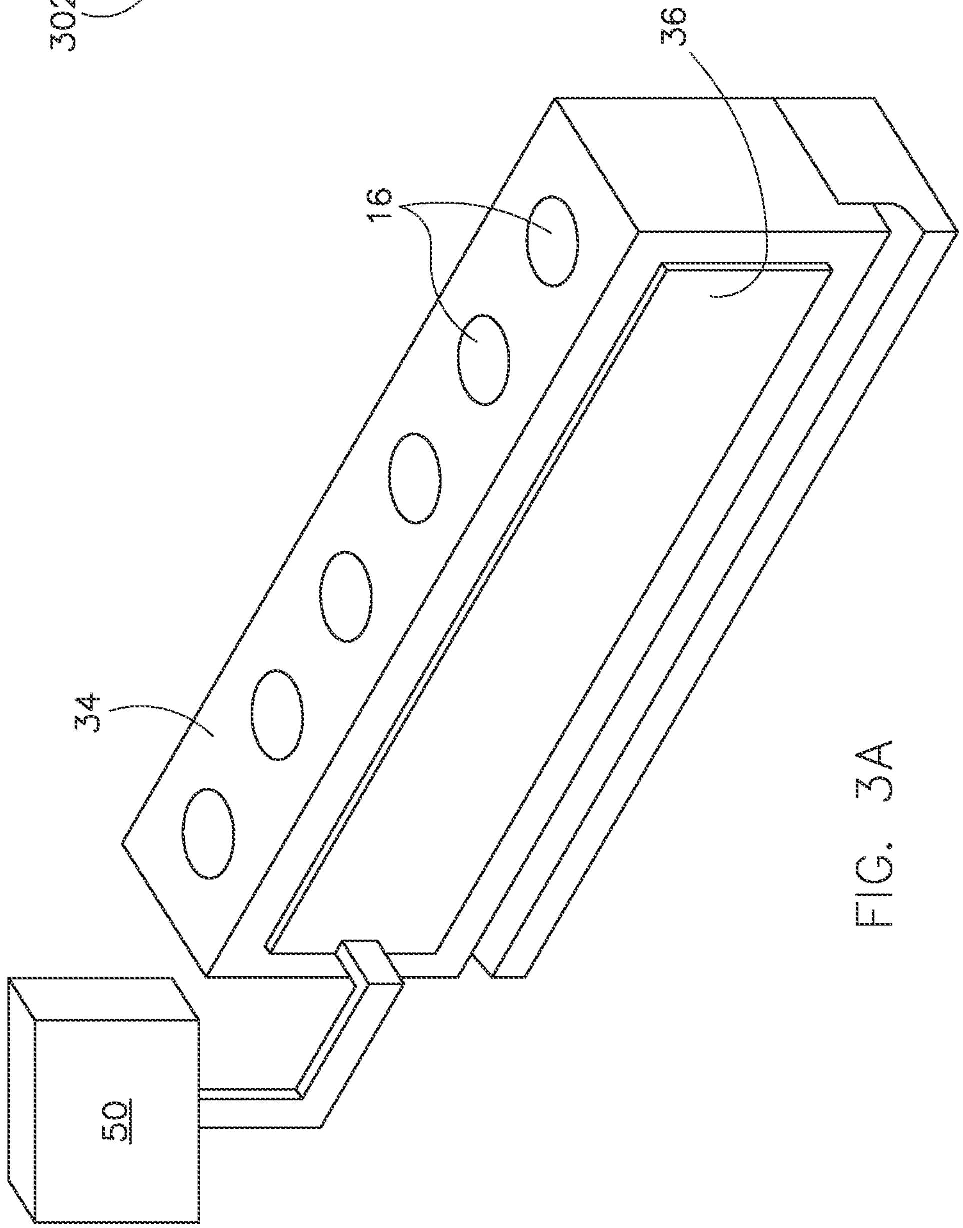
FIG. 3A is a perspective view of one embodiment of a biological indicator reader showing a block of six (6) biological indicator holders and a heater element for heating the same during the sterilization process.

FIG. 3A is a perspective view of an embodiment of a BI holder block 34 of the BI reader 10. In this embodiment, the BI reader further includes a heater subsystem which comprises a heater element 36, an electronic switch, an electronic current measurement circuit, temperature sensors, all connected to an electronic controller system 50, which can be a microprocessor. In one embodiment as illustrated in FIG. 3A, BI holder block 34 of the BI reader includes six (6) BI holders which are heated by heater element 36, which in turn is connected to electronic controller system 50. In some embodiments, the goal of the heater subsystem is to maintain the twelve BI holders at about 60° C. When first powered on at room temperature, the expected time to reach 60° C. is about 30 minutes. Afterwards, the power is left on, and the well temperature remains constant until the BI reader is disconnected from power. Electronic controller system 50, which can be a microprocessor, monitors the well temperature using two temperature sensors and adjusts the current delivered to the heater element 36 to keep the temperature constant. FIG. 3B illustrates an embodiment of heater control. The heater control comprises heater element 302 and heater block 308 placed in the middle of and adjacent two temperature sensors 304, 306. There are two temperature sensors for twelve BI holders, one for each BI reader block; during operation, the two temperature sensors of the BI reader can read the same value. In some embodiments, temperature readings from the two temperature sensors are within 4 degrees Celsius.

Figure 5:
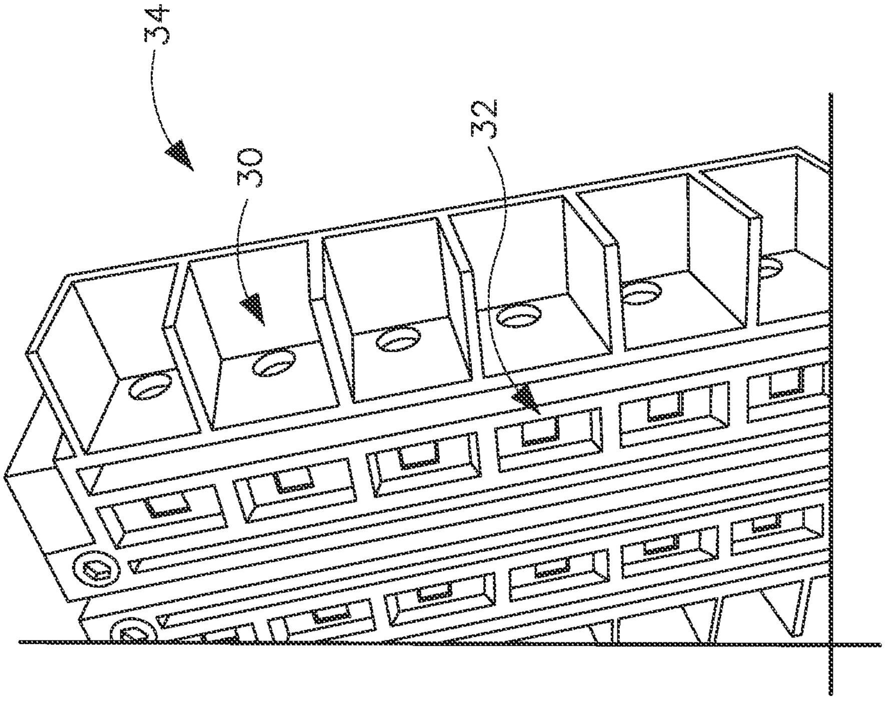
FIG. 5 is a perspective bottom view of a block of biological indicator holders.

As illustrated in FIG. 5, in some embodiments, each BI holder 16 includes a first side aperture 30 and a second aperture 32 at the bottom of the BI holder, which has a square shape here. It will be understood that the apertures can have any shape, for example, round, square, triangular, rectangular, oval or the like. In one embodiment, first side aperture 30 is round and second aperture 32 at the bottom of the BI holder, which has a square shape.

Figure 6:
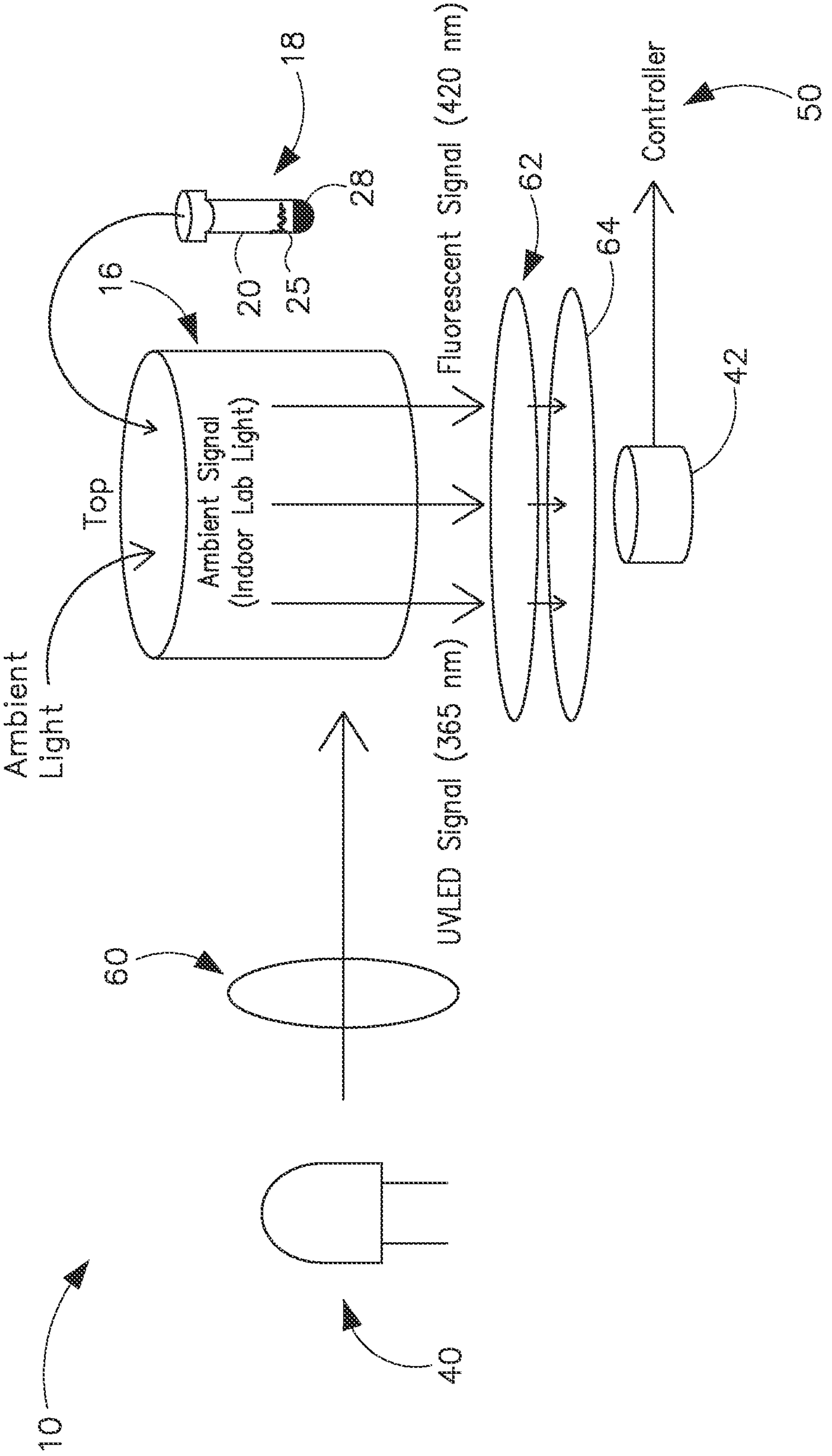
FIG. 6 is a schematic of one embodiment of a biological indicator holder or well of a biological indicator reader.

FIG. 6 is a schematic of one embodiment of BI holder 16 of biological indicator reader 10. Each BI holder 16 has a UV light emitter 40 incident upon the BI container 20 from the side and a single optical detector 42 directly below. In one aspect, the UV light emitter can be a UV light emitting diode (LED) having a wavelength of from about 345 nm to about 425 nm. In one embodiment, the wavelength has a peak power at 365 nm. Each BI holder also comprises a well to receive a biological indicator.

UV light emitter 40 can be used in two ways. In one way, UV light emitter 40 excites the growth media 25 inside the BI container 20 including the excitement of a fluorophore called 4-methylumbelliferone or 4MU to emit a fluorescent light signal. In the second way, the UV light emitter is used to detect when a BI container 20 is placed into BI holder 16. For both functions, the BI reader 10 of this disclosure utilizes only one optical detector 42, for example, a UV photodetector.

Unlike, BI readers in the prior art, the current BI reader, in some embodiments, uses only one photodetector or optical detector and this photodetector or optical detector is positioned at the bottom of the well. In addition, because there is only one photodetector or optical detector per well, in some embodiments, there is likewise only one corresponding aperture at the bottom of each well that allows the transmitted UV light from the activated BI through the aperture and to the photodetector or optical detector. In this way, the BI reader has a reduced number of components compared to conventional BI readers having a plurality of photodetectors or optical detectors per well.

In various embodiments, the geometry of the BI holder allows the same optical detector 42 to sense when a BI container 20 is placed in it. As further illustrated in FIGS. 4C, 5 and 6, the UV light enters the BI holder 16 from the side through first side aperture 30, which has a circular shape, and is incident upon the BI container 20 on the side, near the bottom of the BI container 20 of BI 18. The UV light then passes through the outer sleeve 29 of BI container 20 and is transmitted from the BI carrier 28 (shown in 4C). A portion of the transmitted light then transmits through the bottom of outer sleeve 29 of the BI container 20, through the second aperture 32 (which has a square shape) at the bottom of the BI holder 16 and arrives at the optical detector 42.

Optical detector 42 receives light from three sources, namely, UV light emitter 40, fluorescent light from biological sample, if any, and room light that has leaked through the gap of the wall of BI holder 16 and the BI container 20. In many aspects, optical detector 42 is a UV photodetector and is configured to detect (i) the presence or absence of a BI 18 in the BI holder 16 and/or (ii) any fluorescence emitted by the BI 18.

In various aspects, each BI holder 16 has a dedicated ultra-violet (UV) light emitter 40 with optical wavelength centered at 365 nm. An optical path exists from the UV light emitter 40, through the BI vial, and last to exit to the optical detector 42, which, in many embodiments, is a UV photodiode. To limit the bandwidth of the UV light, a first optical bandpass filter 60 (290 nm to 390 nm) is present in the path of the UV light before it enters the BI holder through first side aperture 30. Each UV optical path is isolated from other UV paths by mechanical design of optical barriers. The intensity of UV light emitted from each UV LED is controlled electronically by an electronic controller system 50. In many aspects, electronic controller system 50 is a microprocessor having a memory coupled to the electronic controller system and configured to receive and store data indicative of the fluorescence of each BI 18 based on fluorescence intensity signals received by electronic controller system 50.

In other aspects, each BI holder 16 is also equipped with optical detector 42, in some aspects, a photodiode that can detect UV signals of 430 nm, that is, the fluorescent signal. The output of each optical detector 42 is transmitted through an analog multiplexer (not shown) then electronically amplified and integrated. The readings from all 12 BI holders are then time multiplexed and fed to the analog-to-digital converter inside the electronic controller system 50, which can be a microprocessor. Electronic controller system 50 can then measure the intensity of each of the fluorescent signals. Each UV photodiode is optically isolated from all others so that there is no overlap of received fluorescent signals. Additionally, each optical detector 42 has two optical filters, a second optical filter 62 and a third optical filter 64 below second optical filter 62 and in the path to optical detector 42 used to limit the bandwidth of the detected signal to a bandpass from about 410 nm to about 560 nm and block the excitation wavelength of 365 nm. In some embodiments, the bandpass is from about 412 nm to about 418 nm. In some aspects, third optical filter 64 is positioned below second optical filter 62. Each UV photodiode also has an o-ring that mechanically seals its top surface to the enclosure to prevent any sterilant ingress.

Figure 8:
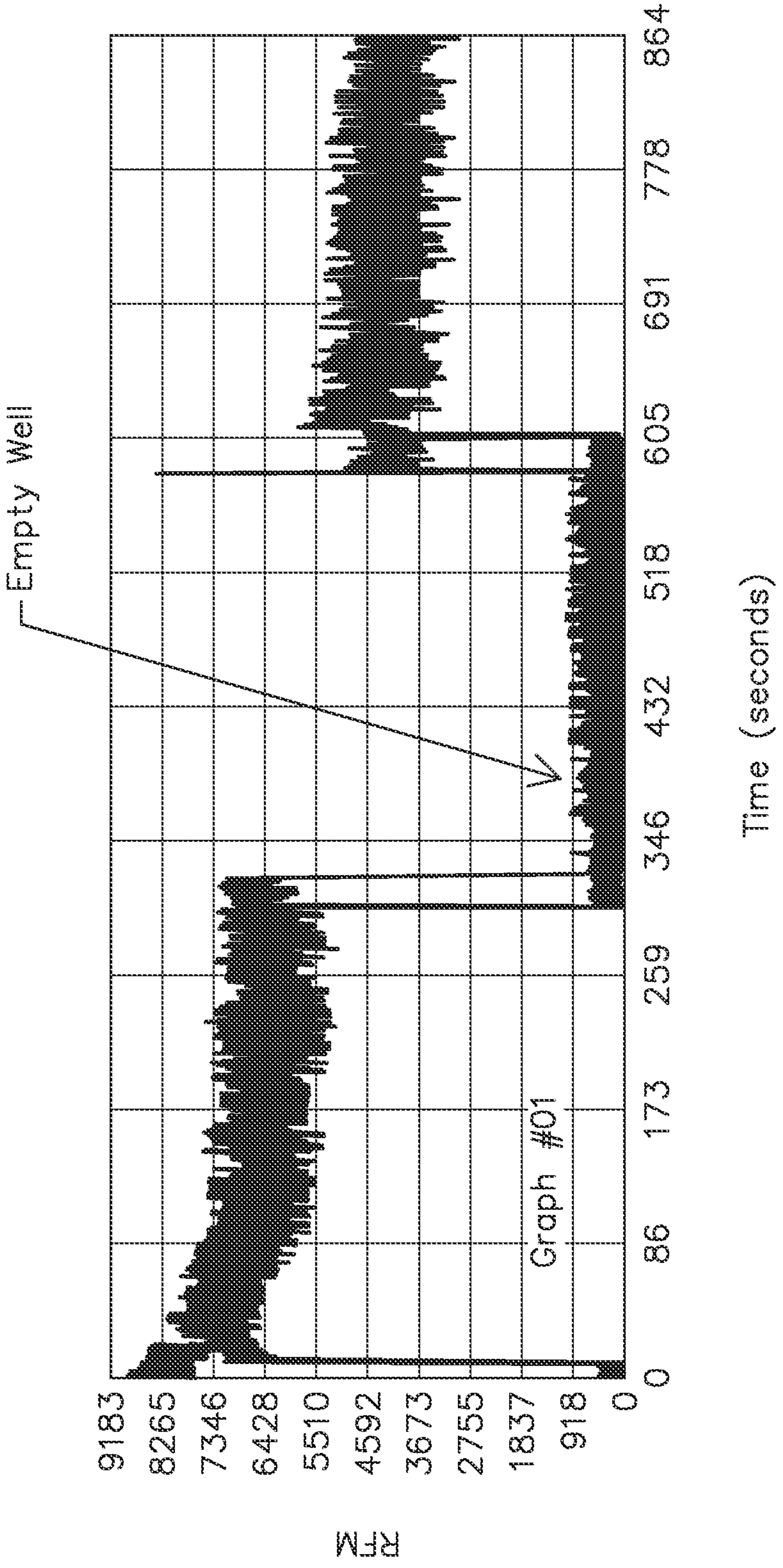
FIG. 8 is fluorescent data taken with the UV LED emitter on and off for an occupied biological indicator and empty biological indicator.

As illustrated in FIG. 8, in one embodiment, data is taken with the UV light emitter 40 on and off. The difference between these two values is used as the measured data. When a crushable ampoule 24 (illustrated in FIG. 4B) is present in BI holder 16, the data values are above 900 relative fluorescent units (RFU). When a BI holder is empty, the data values are below 900RFU In FIG. 8, graph #01 is an embodiment of a data record where the BI holder starts out containing a BI. The BI is then taken out of the BI holder at about 300 seconds and then placed back in the BI holder at about 600 seconds. This graph can be displayed on the BI reader or on a display of a computer linked with the BI reader.

In various aspects, BI reader 10 is controlled by an electronic controller system 50 which is coupled to the optical detector 42. In some aspects, electronic controller system 50 is configured to receive an input signal emitted when optical detector 42 receives light exiting each biological indicator holder 16 and to provide an output signal indicating sterilization process failure or success.

Figure 7:
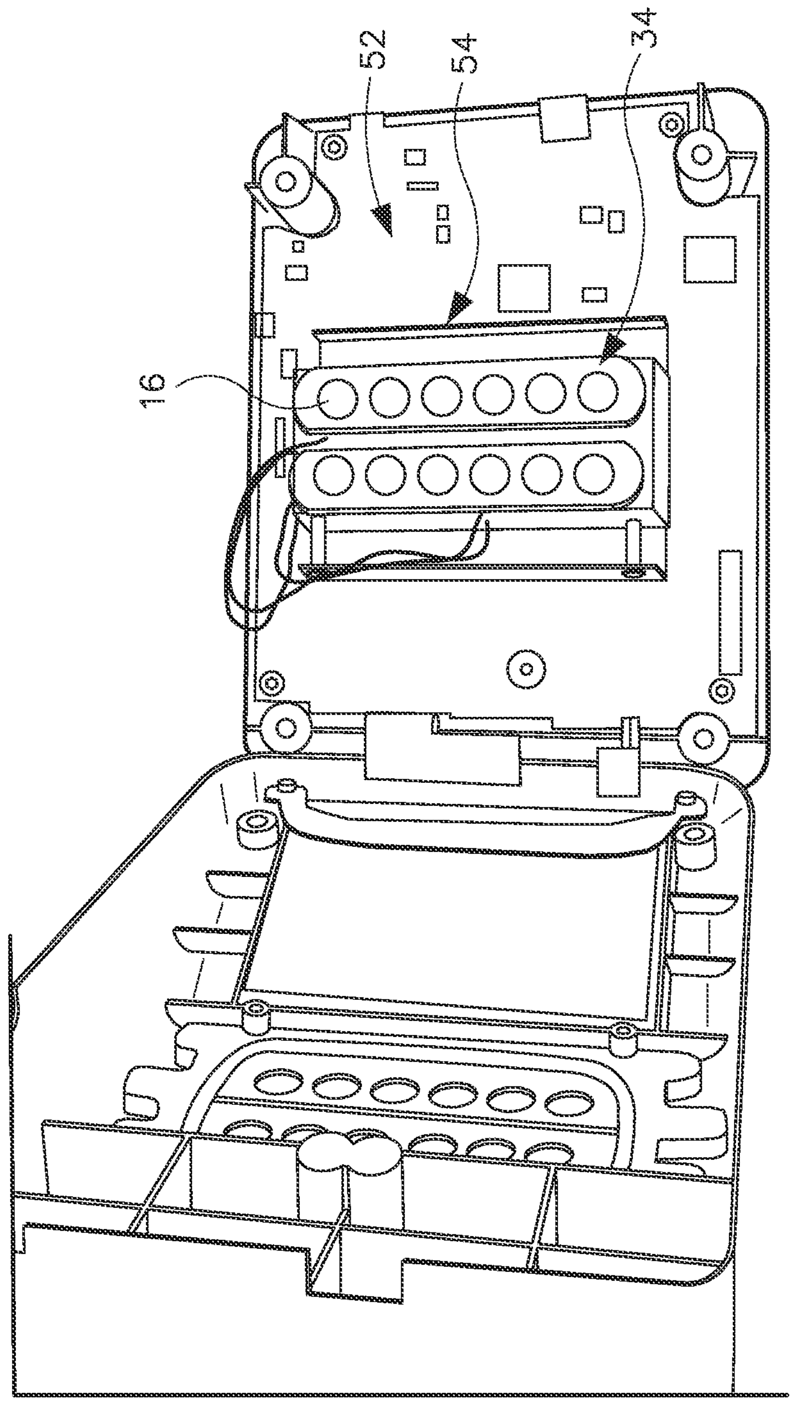
FIG. 7 is a perspective top view of a biological indicator reader.

FIG. 7 illustrates an embodiment of the BI reader 10 wherein the BI reader further comprises a horizontal circuit board 52 positioned under the plurality of biological indicator holders 16 and a vertical circuit board 54 orthogonal to the horizontal circuit board and proximate the biological indicator holders. In this embodiment, UV light emitter 40 is mounted on the vertical circuit board 54 and the optical detector 42 is mounted on the horizontal circuit board 52.

Biological Indicator

A typical biological indicator being used today is a self-contained biological indicator (SCBI), which contains, among other things, microorganisms, culture medium, carrier, and a crushable container (e.g., vial). Examples of various features that may be employed in an example of a BI 18 are described in U.S. application Ser. No. 15/513,887, assigned to SPS medical Supply Corp., NY, USA, which is incorporated herein by reference as if set forth in full. Biological indicators that can also be used in the BI reader of the current application can be obtained from Crosstex International, Inc. Hauppauge, New York, USA.

Figure 9:
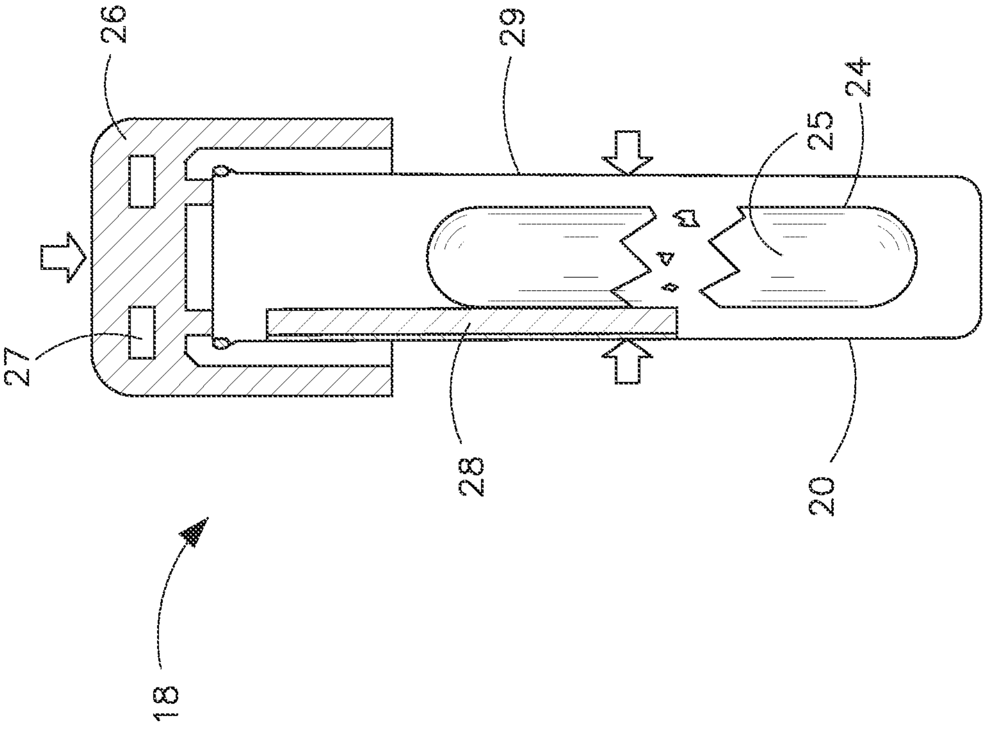
FIG. 9 is a is a front view of one embodiment of the components of the biological indicator.

In various embodiments, BI 18 can be read by BI reader 10. As illustrated in FIGS. 4C and 9, BI 18 has a BI container 20 which comprises a cylindrical outer sleeve 29, a glass media vial or crushable ampoule 24 which comprises growth media 25 (that can have, for example, 4-methylumbelliferyl-α-D-glucopyranoside (MUG) or para-nitrophenol-α-D-glucoside (PNPG)) and a BI carrier 28 for the biological sample or microorganisms, in which the carrier is separated from crushable ampoule 24 but is available within the BI container 20. The BI container 20 is configured to encase or self-contain the multiple components of the biological indicator. In various embodiments, the BI and its components are disposable.

In some aspects, BI container 20 can be made of semi-transparent plastic. In other embodiments, the BI container can be made from other materials. For example, the container comprises a glass, a metal (e.g., foil), a polymer (e.g., polycarbonate (PC), polypropylene (PP), polyphenylene (PPE), polythyene, polystyrene (PS), polyethylene, polypropylene, polyester (e.g., polyethylene terephthalate (PET)), polymethyl methacrylate (PMMA or acrylic), acrylonitrile butadiene styrene (ABS), cyclo olefin polymer (COP), cyclo olefin copolymer (COC), polysulfone (PSU), polyethersulfone (PES), polyetherimide (PEI), polybutyleneterephthalate (PBT)), a ceramic, a porcelain, or combinations thereof.

In various aspects, BI 18 comprises a BI carrier 28 as illustrated in FIG. 9. In the embodiment shown, the BI carrier is shown as 28 and is disposed within the BI container 20. In some embodiments, BI carrier 28 is fixed to a section of container 20. In some embodiments, BI carrier 28 is fixed to the container via a slit in the container, a ledge in the container, a ridge in the container, clips, snaps, adhesive, anchors, buttons, staples, posts, and/or fixation plates. In some embodiments, the carrier is inserted into a bifurcated section of the container. In some embodiments, the carrier is disposed in a breakable chamber of the container separated from another section of the container. In some embodiments, the carrier is freely moving in the container.

In various embodiments, the carrier can be made from a variety of materials. The carrier is configured to be inoculated with a microorganism and other components, for example, a humectant, anti-agglomerating agent or surfactant. The carrier will hold the microorganism and other components on it. The carrier will allow contact with the growth media in the biological indicator after the sterilization procedure so that any surviving microorganisms can grow and/or metabolize the nutrients in the growth media, which will cause a detectable signal that can be read by eye or machine.

Although, in some aspects, the plastic outer sleeve 29 of BI 18 attenuates light intensity, it allows a percentage of light through. Inside the vial, near the bottom, is BI carrier 28 for the biological sample as shown in FIG. 4C. Biological indicator 18 is activated by crushing the crushable BI container 20 with BI crusher 22 prior to insertion into the BI holder 16, wherein fluorescence is detected when a viable enzyme from a viable microorganism digests the culture medium. When UV light shines on biological sample of BI carrier 28, it emits fluorescent light in proportion to the biological population. The fluorescent light then transmits through the bottom of the outer sleeve 29 to the optical detector 42.

In some embodiments, the detection method of the effectiveness of at least a sterilization process may be selected based on the property of interest and may include, for example, fluorometric, visual, pH, and spectroscopic detection methods. The detection of a measurable change in an indicator property within an established period of time indicates viability of microorganisms and inadequate sterilization. The absence of a measurable change within the established period of time demonstrates that the sterilization process was lethal to the test microorganisms and, thus, adequate. In some embodiments, the detection can be determined by measuring turbidity of the growth media by eye or machine.

In one embodiment, the BI growth media 25 contains 4-methylumbelliferyl α-D-glucoside (MUG). MUG is an enzyme substrate. In various aspects, the spores used in BI 18 contain the enzyme α-glucosidase. Any surviving spores will make the α-glucosidase enzyme. When MUG and α-glucosidase contact each other in the BI container 20, α-glucosidase digests the MUG to release a fluorophore called 4-methylumbelliferone or 4MU. Esters of 4-methylumbelliferone (4-MU) do not fluoresce unless cleaved to release the fluorophore. Fluorometric enzyme assays are based on the hydrolysis of 4-MU-containing substrates such as β-4-MU-glucuronide by β-glucuronidase (GUS), or b-4-MU-galactose by β-galactosidase (GAL). Cleavage of 4-methylumbelliferyl-b-D-galactoside by β-galactosidase enzyme yields the fluorescent molecule 4-MU that emits light at 460 nm when excited by 365 nm UV light. In short, when UV light having a wavelength of about 365 nm shines on 4MU, it excites the molecule and causes it to emit light or fluoresce at a specific wavelength about 430 nm. It is the light emitting feature of 4MU that enables a very small amount of it to be detected by a UV light optical detector 42. Detection of a sufficient level of fluorescence during incubation constitutes a positive result, that is, it indicates the presence of viable biological material. A positive result indicates the failure of the associated sterilization process.

In various aspects, with further reference to FIG. 9, each BI 18 comprises a BI container 20 which can have an outer sleeve 29, a crushable ampoule 24 inside the outer sleeve and a cap 26. In some aspects, crushable ampoule 24 can be a vial containing growth media for the microorganisms contained in the outer sleeve 29. Prior to sterilization, the outer sleeve 29 comprises viable microorganisms containing an enzyme and crushable ampoule or vial that contains a culture medium capable of promoting growth of the microorganisms present in outer sleeve 29.

In some embodiments, cap 26 is disposed at an end of BI container 20. In other embodiments, cap 26 is configured to facilitate penetration of the sterilant from the sterilizing chamber into the biological indicator during the sterilization process. In some embodiments, the cap comprises openings, such as, for example, vents 27 and/or slits. In some embodiments, the cap is friction fitted into the end of the biological indicator. In some embodiments, the cap is configured for threaded engagement with the end of the container. In some embodiments, the cap is adhered to the end of the biological indicator via adhesive, clips, snaps and/or flanges. In some embodiments, the cap is made from various materials including, but not limited to polycarbonate, polyolefins, polyamide, polymethacrylates, polymethylpentenes, and/or polyesters.

The culture medium within the crushable ampoule 24 comprises 4-methylumbelliferyl-α-D-glucopyranoside (MUG) or para-nitrophenol-α-D-glucoside (PNPG). In many aspects, crushable ampoule 24 further comprises a pH indicator in the culture medium, which can show a positive indication of spore growth by changing color in the growth media.

In various embodiments, the carrier can be made from a variety of materials. In some embodiments, the carrier can be made from any inorganic material such as silicon including crystalline silicon; various types of glasses including soda-lime, borosilicate glass, phosphate glass, borophosphate glass, boroaluminosilicate glass, or the like; various ceramics which can be defined as earthly raw materials in which silicon and its oxide and complex compounds known as silicates occupy a predominate portion and which have been heated to high temperatures such as structural clay products including tile and terra cotta, various porcelains, porcelain enamels, or the like; metal such as stainless steel, iron, copper; various inorganic substrates containing metalized surfaces such as those immediately set forth, or various metal oxides of groups 4 through 14 of the Periodic Table including titanium oxide, zirconium oxide, iron oxide, copper oxide, aluminum oxide, silica such as quartz, sapphire, and any combination thereof. In some embodiments, the carrier comprises metal oxide.

In various embodiments, the carrier can be made from stainless steel. The stainless-steel carrier is configured to interact with the humectant, anti-agglomerating agent or surfactant, such that microorganisms inoculated onto the carrier will not clump together on the surface of the carrier, thereby causing a uniform distribution of the microorganisms. In some embodiments, an indent is defined within an end of the stainless-steel carrier that is configured for engagement with the microorganisms.

In some embodiments, the carrier can be made from various organic compounds including cellulose in various forms such as paper, filter paper, chromatography paper, blotter paper cardboard, or the like. In some embodiments, the carrier can comprise of polymers, including, but not limited to, acrylic polymers including acrylic acid and acrylate polymers, various polyolefins such as polyethylene and polypropylene, polyvinyl alcohol polymers; polystyrene; and any combination thereof. In various embodiments, the carrier can be made from a combination of inorganic and organic compounds. In some embodiments, the carrier is made from only inorganic compounds. In some embodiments, the carrier is made from only organic compounds.

In some embodiments, the carrier is configured to be inoculated with the microorganism and a humectant, anti-agglomerating agent or surfactant. The carrier will hold the microorganism and the humectant, anti-agglomerating agent or surfactant on it. The carrier will allow contact with the growth media in the biological indicator after the sterilization procedure so that any surviving microorganisms can grow and/or metabolize the nutrients in the growth media, which will cause a detectable signal that can be read by eye or machine.

In some embodiments, the carrier is inoculated with the microorganisms. In various embodiments, the types of microorganisms include, but are not limited to spores, endospores, bacteria, vegetative bacteria, mycobacteria and/or fungi. In some embodiments, the microorganisms include, but are not limited to *Bacillus, Clostridium, Neurospora*, and/or *Candida* species of microorganisms, which are applied to the SCBI.

In various embodiments, *Bacillus* and *Clostridia* species are used to monitor sterilization processes utilizing saturated steam, dry heat, hydrogen peroxide, peracetic acid, ethylene oxide or a combination thereof.

In some embodiments, microorganisms such as *Geobacillus stearothermophilus* and *Bacillus atrophaeus* monitor sterilization conditions. *Geobacillus stearothermophilus* is particularly useful to monitor sterilization under steam sterilization conditions and under hydrogen peroxide sterilization conditions. *Bacillus atrophaeus* is also particularly useful for ethylene oxide and dry heat sterilization. In various embodiments, microorganisms may include bacteria such as *Escherichia coli, Legionella* sp., *Campylobacter* sp., and other enteric bacteria, as BI holder as *Staphylococcus* and *Streptococcus* species and other human pathogenic microorganisms such as *Cryptosporidium.*

In some embodiments, the microorganisms are spores. In various embodiments, the spores comprise *Bacillus, Clostridium, Neurospora, Candida*, and/or *Cryptosporidium*. In some embodiments, the spores comprise *Geobacillus stearothermophilus* and/or *Bacillus atrophaeus.*

In some embodiments, the microorganisms are endospores. In various embodiments, the endospores comprise *Geobacillus stearothermophilus, Bacillus subtilis, Bacillus subtilis globigii, Clostridium sporogenes, Bacillus cereus, Bacillus atrophaeus* and *Bacillus circulans* or a combination thereof.

In various embodiments, the microorganisms are fungi. In some embodiments, the fungi comprise *Aspergillus niger, Candida albicans, Trichophyton mentagrophytes, Wangiella* dermatitis or a combination thereof.

In some embodiments, the microorganisms are mycobacteria. In various embodiments, the mycobacteria comprise *Mycobacterium chelonae, Mycobacterium gordonae, Mycobacterium smegmatis*, and *Mycobacterium terrae* or a combination thereof.

In various embodiments, the microorganisms are vegetative bacteria. In some embodiments, the vegetative bacteria comprises *Aeromonas hydrophila, Enterococcus faecalis, Streptococcus faecalis, Enterococcus faecium, Streptococcus pyrogenes, Escherichia coli, Klebsiella* (*pneumoniae*), *Legionella pneumophila, Methylobacterium, Pseudomonas aeruginosa, Salmonella choleraesuis, Helicobacter pylori,*

*Staphylococcus aureus, Staphylococcus epidermidis*, and *Stenotrophomonas maltophilia* or a combination thereof.

In some embodiments, the carrier is inoculated with one or a combination of the microorganisms. In various embodiments, the carrier comprises the microorganisms at a distal end of the carrier closest to the growth media in the container. In some embodiments, the carrier comprises the microorganisms disposed throughout the carrier.

In one embodiment, the concentration of the microorganisms may be in the range of from about 101 to about 1014 colony forming units (cfu) when disposed on the carrier. In some embodiments, the concentration of microorganisms is in the range from about 104 to about 1010 cfu. In some embodiments, the concentration of microorganisms is in the range from about 106 to about 108 cfu. In some embodiments, the concentration of microorganisms is from about 101, 102, 103 104, 105, 106, 107, 108, 109, 1010, 1011, 1012 1013 or 1014 cfu.

METHODS

This disclosure also provides a method for determining the effectiveness of at least a sterilization process. In many aspects, the method comprises providing a BI reader for reading a plurality of biological indicators to determine the effectiveness of at least a sterilization process. Each biological indicator is configured to exhibit fluorescence when the sterilization process has failed. Each reader comprises a housing having a plurality of biological indicator holders and each holder is configured to receive one of the plurality of biological indicators. Each biological indicator holder has a first aperture on a side and a second aperture on a bottom of the biological indicator holder. The first aperture is positioned to face the UV light emitter and can be round and the second aperture on the bottom of the biological indicator holder and can be square. In many aspects, a heater is coupled to the housing of the BI reader. The heater is configured to heat the plurality of biological indicator holders to a preselected temperature to incubate the biological indicators. In other aspects, a UV light emitter is configured to emit UV light through the first aperture on the side of each biological indicator holder. The BI reader also includes an optical detector positioned under the second aperture on the bottom of the biological indicator holder. The optical detector of the BI reader is configured to detect fluorescence intensity indicating the effectiveness of the sterilization process. The method also includes providing a biological indicator capable of exhibiting fluorescence to indicate the effectiveness of a sterilization process. The biological indicator provided by this method also comprises a crushable container. Upon subjecting of the biological indicator to the sterilization process to obtain a sterilized biological indicator, the crushable container of the sterilized biological indicator can be crushed to activate the indicator. Upon incubating the activated biological indicator in one of the biological indicator holders of the biological indicator at a preselected temperature and for a preselected period of time, the BI will be emitting UV light through the first aperture on the side of each biological indicator holder. A fluorescence intensity will be detected by the optical detector positioned under the second aperture on the bottom of the biological indicator holder indicating the effectiveness of the sterilization process.

In various aspects, the fluorescence intensity is detected when the UV light emitter is on and when the UV light emitter is off, a baseline value for the fluorescence intensity is obtained. When the biological indicator holder is empty, the emitted UV light is below 900 RFU and when the biological indicator is in the biological indicator holder, the emitted UV light is above 900 RFU. In some aspects, the UV light emitter emits UV light at a wavelength from about 290 to about 390 nm. In some embodiments, the wavelength is from about 345 nm to about 425 nm with peak power at 365 nm.

In many aspects, the biological indicator reader further comprises an electronic controller system coupled to the optical detector to receive a signal emitted when the optical detector receives light exiting each biological indicator holder and to provide an output signal indicating sterilization process failure or success. In various aspects, the electronic controller system is a microprocessor having a memory coupled to the electronic controller system and configured to receive and store data indicative of the fluorescence of each biological indicator based on fluorescence signals received by the electronic controller system.

In other aspects, the biological indicator reader further comprises a horizontal circuit board positioned under the plurality of biological indicator holders and a vertical circuit board orthogonal to the horizontal circuit board and proximate the biological indicator holders, wherein the UV light emitter is mounted on the vertical circuit board and the optical detector is mounted on the horizontal circuit board.

In some embodiments, each biological indicator comprises a container having an outer sleeve, a crushable vial inside the outer sleeve and a cap disposed at an end of the container. In some embodiments, the cap comprises vents for allowing inflow of the sterilant into the biological indicator.

In various embodiments, the outer sleeve of the biological indicator comprises viable microorganisms containing an enzyme and the frangible container is an ampoule that contains a culture medium capable of promoting growth of the microorganisms present in the outer sleeve. The culture medium within the ampoule comprises 4-methylumbelliferyl-α-D-glucopyranoside (MUG) or para-nitrophenol-α-D-glucoside (PNPG). Spores surviving the sterilization process produce the enzyme α-glucosidase, which digests MUG or PNPG releasing the fluorescent moiety that can be detected. In some embodiments, the crushable container further comprises a pH indicator in the culture medium.

In various embodiments, the housing of the reader further comprises a crusher disposed proximately to the biological indicator holders, the crusher sized to crush the crushable container and release the culture medium within each biological indicator; a cover for the plurality of biological indicator holders; and a display coupled to the electronic controller system and configured to provide an indication of the effectiveness of the sterilization process associated with each biological indicator.

In some embodiments, the housing further comprises an optical filter disposed above the optical detector and configured to filter light other than wavelengths approximately associated with fluorescence and UV excitation. In many embodiments, the optical detector is a UV photodetector and is configured to detect (i) the presence or absence of a biological indicator in the biological indicator holder and/or (ii) any fluorescence emitted by the biological indicator.

In various embodiments, a method for determining effectiveness of a sterilization procedure with a biological indicator is provided. In various embodiments, the method comprises subjecting the biological indicator to a sterilization cycle, the biological indicator comprising a deformable container having a crushable vial disposed therein comprising growth media and a carrier separated from the crushable vial but within the deformable container; activating the biological indicator by applying pressure to said deformable container to crush the vial so as to allow the growth media and the spores of the carrier to come into contact with each other; and incubating the biological indicator for a predetermined period of time to permit any growth of the spores surviving said sterilization cycle to grow in the growth media, wherein the growth provides a determination of the effectiveness of the sterilization procedure.

In some embodiments, the biological indicator further comprises a vented cap, as described herein, which allows a sterilant from the sterilization procedure to enter the deformable container and contact the spores on the carrier during the sterilization cycle. As the sterilant (e.g., hydrogen peroxide, peracetic acid, etc.) enters through the vented cap, it contacts the microorganisms on the carrier and should be in a sufficient quantity and time to kill all or most of the microorganisms should there be successful sterilization. In this way the object (e.g., instrument, implant, etc.) to be sterilized will be subject to the same successful sterilization procedure.

In some embodiments, the method comprises the biological indicator and all of its components and/or features, as described herein. In some embodiments, the sterilization procedure comprises contacting the spores with hydrogen peroxide sterilization, steam sterilization and/or ethylene oxide sterilization. In various embodiments, the sterilization procedure comprises contacting the spores with hydrogen peroxide sterilization.

In various embodiments, the biological indicator is placed within a sterilization chamber along with objects to be sterilized. During the sterilization cycle, a portion of the sterilant (e.g., hydrogen peroxide, peracetic acid, steam, etc.) permeates through the cap's openings, infiltrating into the container where the sterilant interacts with the microorganism (e.g., spores) inoculated on the carrier.

In some embodiments, after the sterilization cycle has been completed, the biological indicator is activated by squeezing the center, sides and/or the top of the deformable container or inverting it, which causes the crushable vial to break, thereby releasing the growth media contained within the crushable vial. In other embodiments, the biological indicator is activated by crushing the crushable container prior to incubating it in the biological indicator holder. The growth media will then contact the microorganisms (e.g., spores).

The biological indicator is incubated for a predetermined time, in some aspects, 30 minutes, at an appropriate temperature of about 60° C. At the end of the incubation period, a detector, as described herein, is used to determine whether any spores survived the sterilization process. In various embodiments, a positive indication of spore growth is shown via a pH indicator and the pH indicator can change color in the growth media.

Biological Indicator System

A biological indicator system for detecting the effectiveness of a sterilization process is also provided. The BI system comprises a biological indicator reader for reading a plurality of biological indicators to determine the effectiveness of at least a sterilization process, each biological indicator configured to exhibit fluorescence when the sterilization process has failed. The BI reader comprises a housing having a plurality of biological indicator holders, each holder configured to receive one of the plurality of biological indicators, each biological indicator holder having a first aperture on a side and a second aperture on a bottom of the biological indicator holder. The BI reader also includes a heater coupled to the housing and configured to heat the plurality of biological indicator holders to a preselected temperature and a preselected period of time to incubate the biological indicators. The BI reader further includes a UV light emitter configured to emit UV light through the first aperture on the side of each holder; and an optical detector positioned under the second aperture on the bottom of the biological indicator holder, the optical detector configured to detect fluorescence intensity indicating the effectiveness of the sterilization process; and a biological indicator containing a fluorescent moiety, spores, growth media and a crushable container, the biological indicator being sterilizable and configured to receive UV light from the UV light emitter.

Figure 10:
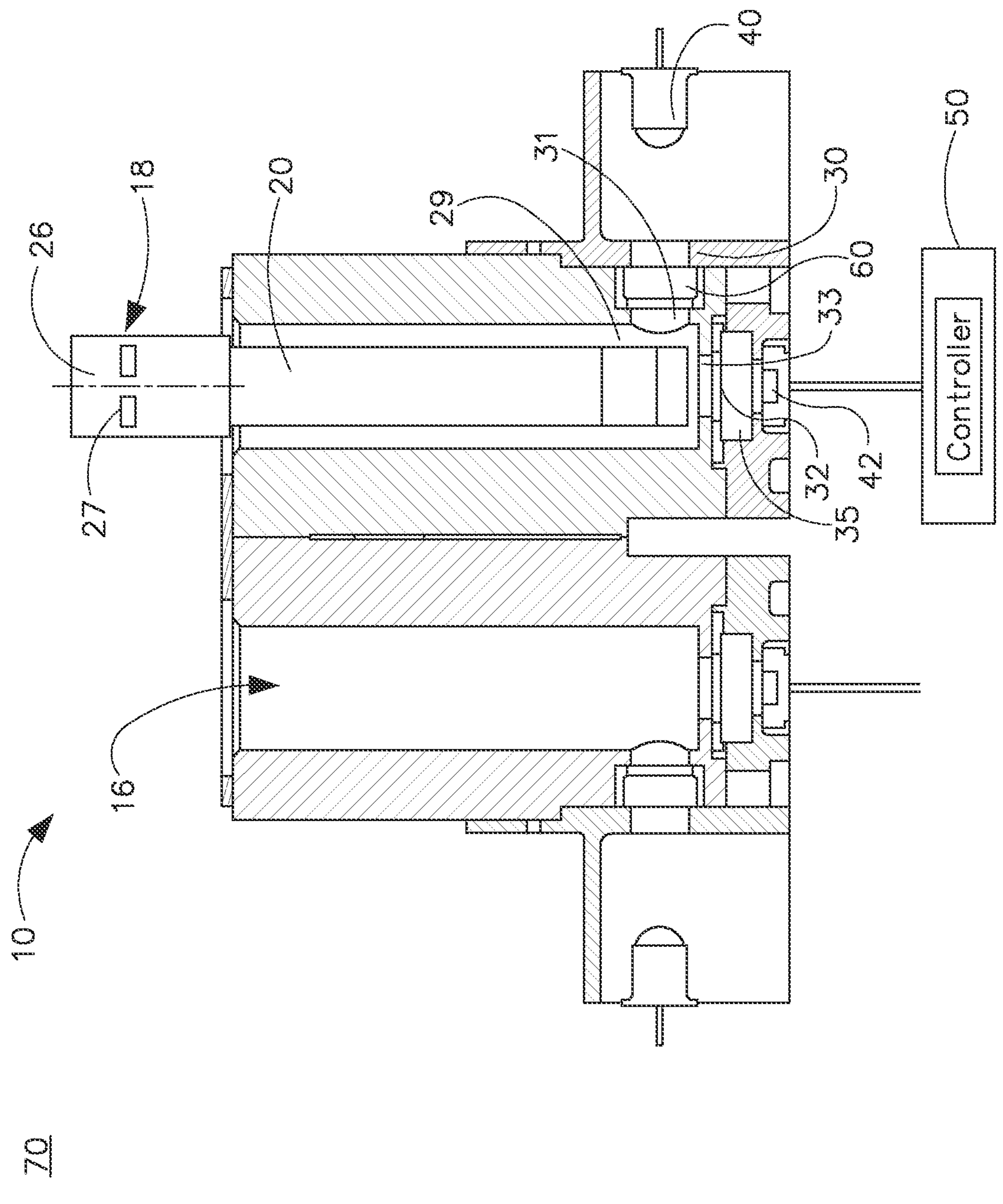
FIG. 10 is a partial cross-sectional side view of a biological indicator system according to an embodiment of the present disclosure, the biological sterilization indicator system including a biological sterilization indicator shown in a perspective view.

FIG. 10 is a partial cross-sectional side view of a biological indicator system according to an embodiment of the present disclosure, the biological indicator system including a biological indicator shown in a perspective view. FIG. 10 illustrates an embodiment of biological indicator system 70 which comprises, consists essentially of or consists of BI reader 10 and BI 18. BI 18 comprises BI container 20 having a cap 26, which cap contains vents 27. BI 18 is located in BI holder 16, which is a well. An empty well is also illustrated in FIG. 10. BI system 70 further includes UV light emitter 40 which is used to excite growth media that can be present inside the BI container 20 to emit a fluorescent light signal. UV light emitter 40 can also be used to detect whether BI container 20 was placed into BI holder 16. For both functions, the BI reader 10 of this disclosure utilizes only one optical detector 42, for example, a UV photodetector. As illustrated in the embodiment of FIG. 10, optical detector 42 is placed directly below the bottom of BI holder 16. As a result, the geometry of the BI holder allows the same optical detector 42 to sense when a BI container 20 of BI 18 is placed in it. As further illustrated in FIG. 10, the UV light from UV light emitter 40 enters the BI holder 16 from the side through first side aperture 30, which has a circular shape in some embodiments, is incident upon the BI container 20 on the side, near the bottom of the BI container 20 of BI 18. In some embodiments, the BI reader further comprises a third aperture 31, which is a well entrance aperture that is disposed between the first side aperture 30, which is also a UV aperture, and the BI container 20. The UV light then passes through the outer sleeve 29 of BI container 20 and is transmitted from the biological sample carrier (not shown). A portion of the transmitted light then transmits through the bottom of outer sleeve 29 of the BI container 20, through the second aperture 32, which has a square shape in some embodiments, at the bottom of the BI holder 16 and arrives at the optical detector 42. In some embodiments, the BI reader comprises a fourth aperture 33. The fourth aperture is a well exit aperture disposed between the second aperture, which is also the optical aperture and the optical detector. In some embodiments, the BI reader further comprises an optical detector filter 35 disposed between the well exit aperture and the optical detector.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A biological indicator system for detecting an effectiveness of a sterilization process, the biological indicator system comprising a biological indicator reader for reading a plurality of biological indicators to determine the effectiveness of at least a sterilization process, each biological indicator configured to exhibit fluorescence when the sterilization process has failed, the biological indicator reader comprising a housing having a plurality of biological indicator holders, each biological indicator holder configured to receive one of the plurality of biological indicators, each biological indicator holder having a first aperture on a side and a second aperture on a bottom of the biological indicator holder; a heater coupled to the housing and configured to heat the plurality of biological indicator holders to a preselected temperature and a preselected period of time to incubate the plurality of biological indicators; an UV light emitter configured to emit UV light through the first aperture on the side of each biological indicator holder; and an optical detector positioned under the second aperture on the bottom of one of the plurality of biological indicator holders, the optical detector configured to detect fluorescence intensity indicating the effectiveness of the sterilization process; a biological indicator containing spores, growth media containing a fluorescent moiety, and a crushable container, the biological indicator being sterilizable and configured to receive UV light from the UV light emitter and a crusher aligned with the plurality of biological indicator holders and that receives the crushable container and, upon movement of the crushable container from a first side of the plurality of biological indicator holders with which the crusher is aligned to a second side of the plurality of biological indicator holders with which the crusher is aligned, crushes the crushable container, thereby activating the biological indicator.

* * * * *